(12) United States Patent
Sharaf et al.

(10) Patent No.: US 6,821,402 B1
(45) Date of Patent: Nov. 23, 2004

(54) SPECTRAL CALIBRATION OF FLUORESCENT POLYNUCLEOTIDE SEPARATION APPARATUS

(75) Inventors: Muhammad A. Sharaf, Oakland, CA (US); Maria C. Roque-Biewer, San Bruno, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 09/154,178

(22) Filed: Sep. 16, 1998

(51) Int. Cl.[7] .................. G01N 27/26; G01N 31/00; G06F 19/00; C12Q 1/68; C12M 1/34

(52) U.S. Cl. .................. 204/461; 204/456; 204/466; 204/606; 204/612; 204/616; 435/6; 435/287.2; 436/8; 250/252.1; 702/19; 702/20

(58) Field of Search .................. 204/606, 607, 204/608, 610, 612, 615, 616, 617, 618, 621, 456, 461, 466, 467; 702/19, 20; 435/6, 287.2; 250/252.1

(56) References Cited

U.S. PATENT DOCUMENTS 5,138,830 A  8/1992  Chen (List continued on next page.)

FOREIGN PATENT DOCUMENTS

| EP | 0 816 837 A1 | 1/1998 |
|---|---|---|
| WO | WO 95/30139 | 11/1995 |
| WO | WO 96/35810 | 11/1996 |
| WO | WO 97/46963 | 12/1997 |

OTHER PUBLICATIONS

US 5,747,249, 5/1998, Smith et al. (withdrawn)
J. Yin et al., "Automated Matrix Determination in Four Dye Fluorescence–Based DNA Sequencing," *Electrophoresis* 17:1143–1150 (1996).

(List continued on next page.)

*Primary Examiner*—Nam Nguyen
*Assistant Examiner*—John S. Starsiak, Jr.
(74) *Attorney, Agent, or Firm*—Scott R. Bortner; Jeffery D. Frazier

(57) ABSTRACT

The invention relates to methods, compositions, and systems for calibrating a fluorescent polynucleotide separation apparatus. One aspect of the invention is multiple color calibration standards and their use. A multiple color calibration standard is a mixture of at least two polynucleotides of different length, wherein each of the polynucleotides is labeled with a spectrally distinct fluorescent dye. Another aspect of the invention is to produce total emission temporal profiles of multiple color calibration standards for use in calibrating fluorescent polynucleotide separation apparatus. The peaks corresponding to the fluorescently labeled polynucleotides in the total emission temporal profile may be detected using a peak detector that is driven by changes in the slopes of the total emission temporal profile. Calibration of fluorescent polynucleotide separation apparatus, with various embodiments of the methods of the invention, includes the step of identification of the labeled polynucleotides of the multiple color calibration standards. The process of spectral calibration of a fluorescent polynucleotide separation apparatus using a multiple color calibration standard may include the step of the estimating (extracting) of the dyes' reference spectra, using information from the peak detection process performed on the total emission temporal profile. Other aspects of the invention include systems for separating and detecting fluorescently labeled polynucleotides, wherein the system is designed for spectral calibration in accordance with the subject calibration methods employing multiple color calibration standards. Another aspect of the invention is methods and compositions for detecting the flow of electrical current through a separation channel of a fluorescent polynucleotide separation apparatus. These methods and compositions employ monitoring dyes. Monitoring dyes are fluorescent dyes that are spectrally distinct from the dye on the polynucleotide intended to convey genetic information, e.g., fluorescent polynucleotide sequencing reaction products.

10 Claims, 1 Drawing Sheet

U.S. PATENT DOCUMENTS

| | | | |
|---|---|---|---|
| 5,365,455 A | * 11/1994 | Tibbetts et al. | 702/20 |
| 5,436,130 A | * 7/1995 | Mathies et al. | 435/6 |
| 5,741,411 A | 4/1998 | Yeung et al. | |
| 5,821,058 A | * 10/1998 | Smith et al. | 435/6 |
| 5,853,979 A | * 12/1998 | Green et al. | 435/6 X |
| 5,871,628 A | * 2/1999 | Dabiri et al. | 204/461 |
| 5,912,118 A | * 6/1999 | Ansorgi et al. | 435/6 |
| 5,928,907 A | 7/1999 | Woudenberg et al. | |
| 5,981,186 A | * 11/1999 | Gabe et al. | 435/6 |
| 6,017,434 A | * 1/2000 | Simpson et al. | 204/612 |

OTHER PUBLICATIONS

W. Huang et al., "A Method to Determine the Filter Matrix in Four–Dye Flourescence–Based DNA Sequencing," *Electrophoresis* 18:23–25 (1997).

K.M. O'Brien et al., "Improving Read Lengths by Recomputing the Matrices of Model 377 DNA Sequencers," *BioTechniques* 24: 1014–1016 (1998).

S. Liu, et al., "Optimization of High–Speed DNA Sequencing on Microfabricated Capillary Electrophoresis Channels," Analytical Chemistry, 71, 566–573 (1999).

M. Giddings, et al., "A Software System for Data Analysis in Automated DNA Sequencing," Genome Research, 8:644–655 (1998), Cold Spring Harbor Laboratories Press.

Y. Cheng, et al., "Charge–Coupled Device Fluorescence Detection for Capillary–Zone Electrophoresis (CCDCZE)," Applied Spectroscopy, vol. 44, No. 5 (1990).

"Power Spectrum Estimation Using the FFT," Numerical Recipes in C: The Art of Scientific Computing, p. 549–558, Cambridge University Press.

E. Thomas, "A Primer on Multivariate Calibration," Analytical Chemistry, vol. 66, No. 15 (1994).

B. Ewing, et al., "Base–Calling of Automated Sequencer Traces Using Phred. I. Accuracy Assessment," Genome Research 8:175–185 (1998), Cold Spring Harbor Laboratory.

C. Allex, et al., "Improving the Quality of Automatic DNA Sequence Assembly using Fluorescent Trace–Data Classifications," Proceedings of the Fourth International Conference on Intelligent Systems for Molecular Biology, 3–14, St. Louis, MO: AAAI Press (1996).

G. Ouchi, "Peak Detection and Integration," The Data File, vol. 9, No. 9 (1991).

G. Ouchi, "How Data Bunching Affects Data Acquisition and Peak Detection," The Data File, vol. 13, No. 9 (1995).

European Search Report, mailed Dec. 2, 2003, for European Application No. 01125166.7–2204.

* cited by examiner

SPECTRAL CALIBRATION OF FLUORESCENT POLYNUCLEOTIDE SEPARATION APPARATUS

FIELD OF THE INVENTION

The invention is in the field of spectral calibration of fluorescence based automated polynucleotide length measurement instruments.

BACKGROUND

Spectral calibration is to estimate reference spectral profiles (reference spectra) of particular fluorescent dyes using the optical measurement system of an automated DNA sequencer or similar fluorescent polynucleotide separation apparatus where the particular dyes will be utilized. The current practice of spectral calibration relies on measuring the spectral profile of each fluorescent dye separately. This approach to spectral calibration of fluorescent polynucleotide separation apparatus results in reduced throughput because it requires N lanes on gel-based instruments and requires N separate runs on capillary-based instrument. As more fluorescent dyes are developed and utilized routinely (N is expected to increase), the spectral calibration of fluorescent polynucleotide separation apparatus becomes more demanding and less efficient under the current practice. Additionally, the amount of computer resources devoted to spectral calibration also increases with the number of dyes and separation channels analyzed.

SUMMARY

The invention relates to methods, compositions, and systems for calibrating a fluorescent polynucleotide separation apparatus. Fluorescent polynucleotide separation apparatus, such as an automated DNA sequencer, must be spectrally calibrated for use with the different fluorescent dyes to be used in conjunction with the separation system.

One aspect of the invention is multiple color calibration standards and their use. A multiple color calibration standard is a mixture of at least two polynucleotide of different length, wherein each of the polynucleotide is labeled with a spectrally distinct fluorescent dye. In a preferred embodiment of the invention, the multiple color calibration standard comprises at least four polynucleotides of different length, and each of the polynucleotides is labeled with a spectrally distinct dye. The invention includes numerous methods of spectrally calibrating a fluorescent polynucleotide separation apparatus with a multiple color calibration standard.

Another aspect of the invention is to produce total emission temporal profiles of multiple color calibration standards for use in calibrating fluorescent polynucleotide separation apparatus. A total emission temporal profile is a sum of the intensities of the fluorescence signal obtained in all spectral channels as a function of time. The peaks corresponding to the fluorescently labeled polynucleotides in the total emission temporal profile may be detected using a peak detector that is driven by changes in the slopes of the total emission temporal profile. Calibration of fluorescent polynucleotide separation apparatus, with various embodiments of the methods of the invention, includes the step of identification of the labeled polynucleotides of the multiple color calibration standards. The process of spectral calibration of fluorescent polynucleotide separation apparatus using a multiple color calibration standard may include the step of the estimating (extracting) of the dyes' reference spectra, using information from the peak detection process performed on the total emission temporal profile.

Other aspects of the invention include systems for separating and detecting fluorescently labeled polynucleotides, wherein the system is designed for spectral calibration in accordance with the subject calibration methods employing multiple color calibration standards.

Other aspects of the invention include systems for separating and detecting fluorescently labeled polynucleotide, wherein the system is designed for spectral calibration in accordance with the subject calibration methods employing multiple color calibration standards. The subject systems comprise a fluorescent polynucleotide separation apparatus and a computer in functional combination with the apparatus.

Another aspect of the invention is methods and compositions for detecting the flow of electrical current through a separation channel of a fluorescent polynucleotide separation apparatus. These methods and compositions employ monitoring dyes. Monitoring dyes are fluorescent dyes that are spectrally distinct from the dye on the polynucleotide intended to convey genetic information, e.g., fluorescent polynucleotide sequencing reaction products.

DEFINITIONS

Figure 1:
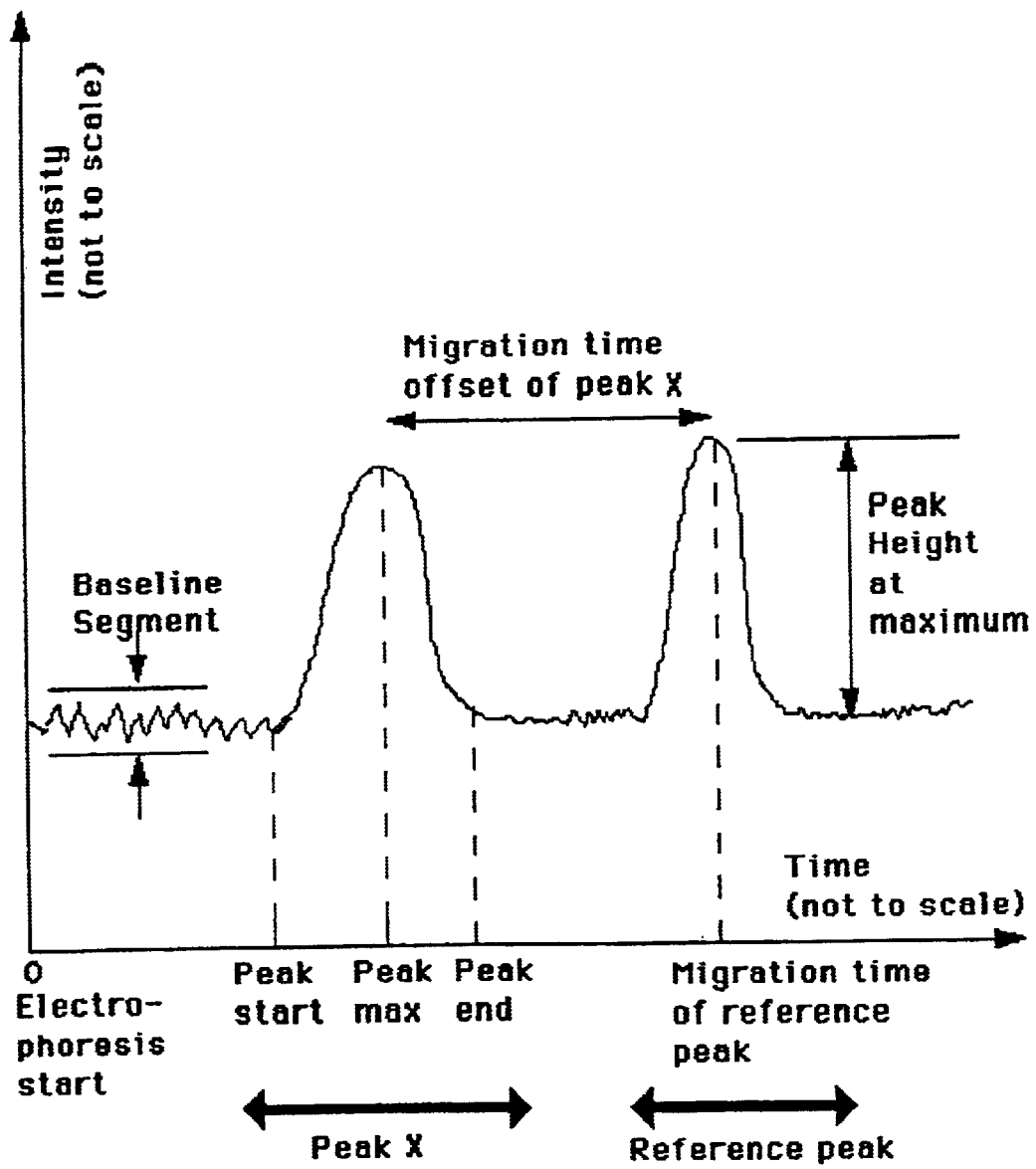
FIG. 1 is diagram of an example of a portion of a temporal profile labeled as to show examples of some of the terms used herein.

The term "fluorescent polynucleotide separation apparatus" as used herein denotes an apparatus for separating fluorescently labeled polynucleotide mixtures (e.g. by electrophoresis) and detecting the separated polynucleotides by the fluorescence emission produced from exciting the fluorescent dye. Examples of fluorescent polynucleotide separation apparatus include automated DNA sequencers such as the PE Applied Biosystems 310 and 377 (Foster City, Calif.). Examples of fluorescent polynucleotide separation apparatus are also described in , among other places, U.S. Pat. Nos. 4,971,677; 5,062,942; 5,213,673; 5,277,780; 5,307,148; 4,811,218; and 5,274,240. The term fluorescent polynucleotide separation apparatus also includes similar instruments for polynucleotide fragment length analysis that are not capable of the single base pair resolution required to obtain DNA base sequence information. Fluorescent polynucleotide separation apparatus comprises one or more separation regions or channels, typically the path of electric current flow in electrophoretic separation devices. Types of separation channels include capillaries, microchannels, tubes, slab gels, and the like. Fluorescent polynucleotide separation apparatus collect several types of data during their operation. This data includes spectral data and temporal data relating to the fluorescent labeled polynucleotides separated by the apparatus. Typically, such data is collected by a detector (e.g. a CCD array, photomultiplier tubes, and the like) designed to obtain quantitative spectral data over a predetermined region or regions of the separation channels. Spectral data collected by the apparatus includes the intensity of fluorescence at a plurality of wavelengths. The different wavelengths sampled are referred to as bins or channels. The apparatus also collects temporal data that is correlated with the spectral data. The temporal data is collected at numerous different time points. For example, a detector at a fixed position will measure increases and decreases in fluorescence intensity as a function of time as a labeled polynucleotide peak passes by the detector. This temporal data may be expressed as "frame" or "scan" number to indicate the different temporal sampling points.

A temporal profile is a plot of the intensity of a spectral signal as a function of time or scan/frame number. A temporal profile consists of systematic and random variations. Systematic variations are caused by peaks, spikes and background drifts. These variations cause the shape of the profile to undergo specific, and often predictable, changes. By contrast, random variations do not cause specific or predictable changes in the temporal profile. A temporal profile has segments that correspond to baseline (baseline segment) and segments that correspond to peaks (peak segments), and segments that correspond to spikes. Baseline segments are made of random variations superimposed on offset value(s).

An emission temporal profile is a plot of the intensity of the signals obtained in a certain spectral channel/bin as a function of time or scan/frame number.

A total emission temporal profile is a plot of the sum of the intensities of the signals obtained in all spectral channels/bin as a function of time or scan/frame number.

The analytical background of a temporal profile is the average of the signals obtained along a segment of the profile where the segment is void of peaks, spikes and systematic variations (i.e., a baseline segment.) This is schematically shown in FIG. 1. The analytical noise of a temporal profile is the standard deviation of the signals obtained along a segment of the profile where the segment is void of peaks, spikes and systematic variations. Analytical background and noise may change as a function of time along the temporal profile. This occurs when there are drifts in the background.

The term net analytical signal refers to the intensity at any point of a profile after correcting for background and baseline offsets and/or drifts. The analytical signal to noise ratio (S/N) is the ratio of the net analytical signal to the analytical noise. Net analytical signals may, or may not, be significant depending on their S/N's.

A peak detector is a mathematical transformation of a profile (e.g. a temporal profile) whose purpose is to locate peaks along the profile. A peak detector is defined by the type of the transformation, and the detection parameters associated with its operation. A typical peak detector distinguishes between segments of a profile that represent baseline (an offset with random noise) and other segments that represent peaks and spikes based on the slope of the temporal profile. From the peak detector's point of view, a baseline segment is a set of data points along the temporal profile where the absolute value of the slope of the profile does not exceed the peak detector's threshold. An ideal peak detector ignores baseline and spike segments, and retains information relevant only to peaks (in our case the component polynucleotides of the multiple color calibration standard.)

Peak slope threshold is a value which if exceeded by the slope of a temporal profile, the presence of a potential peak is indicated. This value may be referred to as the "threshold" parameter of the peak detector. If a peak is actually present, the threshold value is also used to indicate that the temporal profile has returned to baseline levels and that the peak has ended.

Peak start is the first point along the peak segment of a temporal profile. A peak start may be found at baseline levels, or in the valley between two peaks. Peak end is the last point along the peak segment of a temporal profile. A peak end may be found at baseline levels, or in the valley between two peaks. Peak maximum is a point along the peak segment of a profile where the highest intensity is found. Peak width is the number of data points between the start of the peak and the end of the peak (see FIG. 1.) The peak width attribute is helpful in discriminating between peaks that correspond to labeled DNA fragments and spikes. The latter have relatively smaller peak widths.

Peak height at maximum is the intensity at peak maximum corrected for the analytical background (see FIG. 1.) Peak S/N ratio refers to the ratio of the peak height at maximum to the analytical noise of the temporal profile. A peak's S/N attribute is an effective parameter that is used to retain the peak information of the dye-labeled fragments of the multiple color calibration standard.

Migration time of a peak is the time elapsed from the start of the electrophoresis to peak maximum. A particular peak corresponding to a certain labeled polynucleotide of the multiple color calibration standard may serve as a reference peak whose migration time is a reference point from which the migration time of other peaks are measured.

Migration time offset is the difference between the migration time of a particular peak and the migration time of the reference peak (see FIG. 1.) Peaks to the left of the reference peak will have negative migration time offsets, while those to the right of the reference peak will have positive migration time offsets. Reference peaks are located based on rank or migration time. Subsequently, migration time offsets are used to locate all other dye-labeled fragments.

Input parameters are attributes that are used by a particular implementation of the algorithm. These parameters may be specific to the multiple color calibration standard as well as to the platform being used. The implementation attributes may include the peak width, the threshold variable, the peak S/N ratio, the reference peak locator (migration time vs. rank), the migration time offsets, and the appropriate tolerances, if necessary, to account for instrumental and experimental variations.

The term "polynucleotide" as used herein refers to naturally occurring polynucleotides such as DNA and RNA and to synthetic analogs of naturally occurring DNA, e.g. phosphorothioates, phosphoramidates, peptide nucleic acids (PNAs), and the like. The term "polynucleotide" does not convey any length limitation and should be read to include in vitro synthesized oligonucleotides.

SPECIFIC EMBODIMENTS OF THE INVENTION

The invention relates to methods, compositions, and systems for calibrating a fluorescent polynucleotide separation apparatus. Fluorescent polynucleotide separation apparatus, such as an automated DNA sequencer, must be spectrally calibrated for use with the different fluorescent dyes to be used in conjunction with the separation system. Spectral calibration may also be used to account for variations between individual fluorescent polynucleotide separation apparatus and account for changes that occur in a given instrument over time. Fluorescent dyes have characteristic emission spectra for a given excitation wavelength. When multiple different dyes are present in a mixture for separation, the individual contributions of the different dyes to a spectral detection reading must be separated from one another. Such separation may be achieved through the use of a matrix containing spectral emission data of the various dyes used for analysis, see Yin et al., *Electrophoresis* 17:1143–1150 (1996) and U.S. patent application Ser. No.

08/659,115, filed Jun. 3, 1996. The generation of a spectral calibration data matrix for calibrating a fluorescent polynucleotide separation apparatus typically includes the steps of introducing a fluorescent polynucleotide calibration standard into a fluorescent polynucleotide separation apparatus, separating the labeled polynucleotides from each other, and detecting the separated polynucleotides with a detector. The detector collects spectral information relating to the concentration of labeled polynucleotides at a specific location (or locations) on the apparatus. The information collected is the fluorescent emissions at a plurality of wavelengths, (e.g. bins/channels). The information obtained by the detector includes the recording of temporal data (e.g. scan number, for a fluorescent polynucleotide separation apparatus that employs a scanning detector) correlated with the spectral emission data for the measured time points.

One aspect of the invention is to produce total emission temporal profiles of multiple color calibration standards for use in calibrating fluorescent polynucleotide separation apparatus. A total emission temporal profile is a sum of the intensities of the fluorescence signal obtained in all spectral channels as a function of time. Peaks corresponding to the different oligonucleotides in the multiple color calibration standard may then be determined by analyzing the total emission temporal profile with a peak detection transformation function. A reference spectrum for each of the fluorescent dyes of interest used in the multiple color calibration standard may then be produced by selecting a reference spectrum that substantially corresponds to the relevant peak of the total emission profile.

Other aspects of the invention are multiple color calibration standards and their use. A multiple color calibration standard is a mixture of at least two polynucleotides of different length. (It will be understood by persons skilled in the art that each polynucleotide is present in a large number of essentially identical copies so as to provide useful amounts of the subject compositions) Preferably, the length (in number of bases) of each labeled polynucleotide is known precisely so as to maximize the accuracy of the standard. Each of the different length polynucleotides in the standard is labeled with a different fluorescent dye. The predetermined correlation between the length of the given polynucleotide and the particular fluorescent dye that is attached to that polynucleotide is used to identify the polynucleotide of the multiple color calibration standard during the calibration process. The different fluorescent dyes are selected so as to have distinctive spectral profiles (for the same excitation frequency). Preferably the sizes of the polynucleotides in the multiple color calibration standard are selected so as to ensure sufficient separation between the polynucleotides labeled with different dyes such that the spectral profile peaks of the fluorescent dyes do not significantly overlap. In other words, there is preferably sufficient difference between the lengths of the constituent polynucleotides so that for any given polynucleotide peak that is being detected, the possibility that the fluorescence intensity readings are the result of multiple different dyes is minimal.

The sizes of the polynucleotides that are in multiple color calibration standards are selected so as to be within the size separation for the particular fluorescent polynucleotide separation apparatus for which they are designed to be used. Exemplary of such a range is about 10–1500 bases in length, preferably about 10–1000 bases in length, more preferably about 20–500 bases in length. Preferably polynucleotides in the standard are separated by at least 10 bases in length. Methods of making the polynucleotide components of the subject standards are well known to persons of ordinary skill in the art. Such methods include the complete in vitro synthesis of the polynucleotide, e.g. through the use of phosphoramidite chemistry. Alternatively, the polynucleotides may be synthesized enzymatically. For example a PCR (polymerase chain reaction) amplification may be performed using primers separated by the desired distance, wherein one of the amplification primers is labeled with a fluorescent dye of interest.

In preferred embodiments of the invention, the multiple color calibration standard comprises at least four polynucleotides of different length, and each of the polynucleotides is labeled with a spectrally distinct dye. The use of four spectrally distinct dyes, each being essentially the same as the dyes used for producing polynucleotide sequencing reaction products is of particular interest for use in four color chain termination type sequencing (employing either fluorescently labeled chain terminating nucleotides or fluorescently labeled primers). The multiple color calibration standard may comprise one or more fluorescent dyes in addition to the dyes in the standard that correspond to the dyes used in sequencing reactions that are designed for use in conjunction with the particular standard. These additional dyes may be "signal dyes" as described later in this application. These additional dyes, which are preferably attached to polynucleotides, may be used to monitor the electrical current flow through the separation channel or channels of a fluorescent polynucleotide separation apparatus. While detection of electrical current flow through a fluorescent polynucleotide separation apparatus without the use of additional dyes is relatively simple for apparatus employing a single separation channel, e.g. a slab gel, the detection of current through a multi-channel system, e.g., a multiple capillary system, is difficult without using additional dyes. The movement of these additional dyes, which should also be added to the sample for analysis, through the fluorescent polynucleotide apparatus may be detected in order to verify the flow of electrical current through a separation channel, e.g. an individual capillary.

The invention also includes kits for performing the subject method. The kits comprise the individual fluorescently labeled polynucleotide components of the subject multiple color spectral calibration standards. By providing the individual components of a standard, end users may conveniently produce their own standard for specific applications.

A wide variety of florescent dyes may be used to label the polynucleotides in multiple color calibration standards. Fluorescent dyes are well known to those skilled in the art. Examples of fluorescent dyes include fluorescein, 6-carboxyfluorescein, 2',4',5',7',-tetrachloro-4,7-dichlorofluorescein, 2',7'-dimethoxy-4',5'-6-carboxyrhodamine (JOE), N',N',N',N'-tetramethyl-6-carboxyrhodamine (TAMRA) and 6-carboxy-X-rhodamine (ROX). Fluorescent dyes are described in, among other places, U.S. Pat. No. 4,855,225; Menchen et al, U.S. Pat. No. 5,188,934; Bergot et al, International Application PCT/US90/05565; Haugland, R. P., *Handbook of Fluorescent Probe and Research Chemicals*, 6th edition (1996) and like references. Methods of attaching fluorescent dyes to polynucleotides are also well known to those skilled in the art. Examples of such attachment methods can be found in, among other places, U.S. Pat. Nos. 4,789,737; 4,876,335; 4,820,812; and 4,667,025.

The multiple color calibration standards of the invention may also comprise various other components in addition to fluorescent labeled polynucleotides. Such additional components may be used to improve the movement of the polynucleotide through a separation channel of a fluorescent polynucleotide separation apparatus. Examples of additional components include, but are not limited to, buffers, denaturants, and the like.

The invention includes numerous methods of spectrally calibrating a fluorescent polynucleotide separation apparatus with a multiple color calibration standard. A multiple color calibration standard is introduced, i.e., loaded, into a fluorescent polynucleotide separation apparatus. The introduction of a multiple color calibration standard into a florescent polynucleotide separation apparatus and the subsequent separation of the components of the standard along with the collection of the spectral and temporal data obtained from detecting the separated labeled polynucleotides may be conveniently referred to as producing a spectral calibration run. Spectral calibration runs may be performed on a single separation channel or may be simultaneously performed on several separation channels.

A spectral calibration run produces data that can conveniently be analyzed in the form of a matrix, D, with R rows and C columns, that contains the measured intensities in each spectral channel/bin (the columns of the data matrix) as a function of time or frame/scan number (the rows of the data matrix). Each of the C columns represents an emission temporal profile for the corresponding spectral channel/bin. Each of the R rows represent the spectrum acquired during the corresponding data collection/acquisition period. The person of skill in art may devise numerous equivalent representations of the data obtained from a calibration run rather the specific matrix described above, e.g. the components of the rows and columns may be transposed or the data may be manipulated without the use of a 2-D matrix. Each temporal profile contains peaks of different shapes that correspond to the dye-labeled polynucleotides of the multiple color calibration standard. The shape of each of these peaks depends on the emission characteristics of the corresponding dye at the specific spectral channel/bin represented by the temporal profile. A total emission temporal profile may then be prepared by summing the intensities of the signals obtained for all spectral channels/bins as a function of the temporal parameter, e.g. scan/frame number. Ideally, the emission temporal profiles for the labeled polynucleotides of a multiple color spectral calibration standard are "parallel." In practice, however, this ideal property may show deviations that are caused by heterogeneous emission efficiencies, baseline drifts, minor spectral measurements anomalies and deviations from the analytical linear dynamic range. Despite sharing important general properties (peaks of multiple color spectral calibration standard constituent labeled polynucleotide separated by baseline segments,) the temporal profiles of the individual spectral channels/bins may exhibit large variations in S/N ratios, noise distribution as well as peak shapes. In order to minimize such problems, total emission temporal profiles may be used for calibration rather than individual emission temporal profiles. An advantage of total emission profiles is the inclusion of all polynucleotide components of the standard regardless of differences in emission intensities between the spectral channels/bins. The total emission profile, thus, provides a temporal profile that contains all the peaks of the multiple color spectral calibration standards labeled polynucleotide, and only one set of detection input parameters is necessary.

The peaks corresponding to the fluorescently labeled polynucleotide in the total emission temporal profile may be detected using a peak detector that is driven by changes in the slopes of the total emission temporal profile. When the slope of the total emission temporal profile exceeds a certain threshold, the start of a potential peak is detected. The potential peak may then be traced through its crest/maximum and until the potential peak ends, by either having the total emission temporal profile returns to background levels, or detecting the start of another peak. The information regarding the start, maximum and end of the potential peak may then be evaluated to assess the significance of the peak. Only significant peaks (in terms of the minimum requirements indicated by the peak width and peak S/N ratio input parameters) are used to select reference spectra. This process may be used to reject spikes and insignificant/non-target peaks while retaining the peaks corresponding to the components of the multiple color calibration standard.

Peak Detection Transformation

Peak detection is performed on a total emission temporal profile. A preferred transformation to detect peaks is the slope of the total emission temporal profile, and is given as:

$$S_i = (I_{i+1} - I_i) + (I_{i+2} - I_{i-1}) \quad (1)$$

where $S_i$ is the slope (as estimated by the detection transformation) at point i, and $I_k$ is the intensity of the total emission temporal profile at point k. However, other peak detection transformations based on changes of intensity may also be used in the subject methods.

Statistical Distribution of Detection Transformation and Failure Analysis

The threshold parameter used in a peak detector may be an actual value for the slope. However, in a preferred embodiment of the invention the threshold is determined by the distribution of the peak detection transformation based on a probabilistic model. An input variable is used to estimate the threshold. The detection transformations produce a parameter, for example S in Equation 1, that is used for peak detection. The performance of S in distinguishing baseline segments from peak segments in a temporal profile is highly influenced by the distribution of S when I is subjected to random variations only. The variance in S can be estimated by applying error propagation theory to Equation 1, and is given according to:

$$\sigma^2(S) = \Sigma\{[\partial F(S)/\partial I_k]^2 \sigma^2(I_k)\}$$

where F(S) is the detection transformation (Equation 1). For independent measurements, the above expression reduces to:

$$\sigma^2(S) = 4\sigma^2(I) \quad (2)$$

Thus, segments of a temporal profile that correspond to baselines with random variations are expected to produce amplified variations, according to Equation 2, after the detection transformation.

The start of a peak is considered the first data point along the peak segment of the total emission profile that does not belong in the baseline population. The baseline segment's population produces a transformation distribution with a variance of $4\sigma^2(I)$ (Equation 2). The S distribution's variance can, therefore, be used to set-a detection threshold with a probability of failure (incorrectly classifying a data point from the baseline population as the start of a peak segment) that is given as $$Pr[|S_i - \mu(S)| \geq k\sigma(S)\_] \leq k^{-2} \quad (3)$$

where $\mu(S)$ is the mean of the S distribution, and is expected to be zero.

For example if the threshold is set at $3\sigma(S)$, The probability of selecting a data point from the baseline segment's population as a peak start is, according to Equation 3, 100/9 or about 11%. (Equation (3) does not assume a Gaussian, or any other, distribution of the baseline data points population.) To decrease the probability of failure, the threshold may be increased, or one may consider the peak start as two consecutive data points whose transformation exceeds the threshold value. If the threshold is set, again, at $3\sigma(S)$, the probability of $S_i$ exceeding this value at two consecutive measurements when only random variation are present is about 1%. The peaks corresponding to the labeled polynucleotides of the multiple color calibration standards are expected to be among the peaks with the highest peak S/N ratios. Since all detected peaks may be subjected to additional criteria such as minimum peak S/N ratio and minimum peak width, false peak starts (detected-with a probability of 1% as outlined above) are not expected to cause any significant problems in detecting and retaining the peaks corresponding to the labeled polynucleotides of the multiple color calibration standards while rejecting spikes and other non-target peaks.

The outcome of the peak detection process is a set of attributes for all peaks that satisfy the minimum peak width and the minimum peak S/N ratio requirements. This information includes the data point at the start of the peak, the data point at the end of the peak. Appropriate descriptors indicating whether the peak start point is at baseline levels or in a valley between two peaks are also compiled during the peak detection process. Similarly, peak end points are flagged as either being at baseline levels or in a valley between two peaks. Peak information also includes the data point at which the peak maximizes, and the intensity at the peaks' maxima as well as the actual peak width. Where available, the locations of baseline segments to the left of the peak start and to the right of the peak end may also be compiled.

Identification of the Components of Multiple Color Calibration Standards

Calibration of fluorescent polynucleotide separation apparatus with various embodiments of the methods of the invention include the step of identification of the labeled polynucleotides of the multiple color calibration standards. The identification of the colored ladder fragments refers to the assignment of each labeled polynucleotide in a multiple color calibration standard to one of the peaks retained by the peak detector. Assignment can be accomplished by a variety of methods. Since the spectral calibration of fluorescent polynucleotide separation apparatus is accomplished under controlled conditions (known and prespecified materials and experimental parameters), an efficient way to identify the labeled polynucleotides of the multiple color calibration standards is to take advantage of the controlled experimental conditions and the design of the colored ladder. For example, the multiple color spectral calibration standard design may be such that the fragment labeled with the dye DR110 in a multiple color calibration standard has the largest migration time. Under optimized and controlled experimental conditions, where the peak width and peak S/N ratio parameters allow multiple color calibration standard constituent polynucleotides to be detected and retained, the last peak would be the DR110-labeled fragment. A peak with such a high probability of being detected may serve as a reference peak to locate peaks corresponding to the other labeled polynucleotides of the multiple color calibration standard. Since the migration of a labeled DNA fragment is influenced primarily by the size of the DNA fragment, the labeling dye and the separation matrix, migration time offsets over a short migration interval are effective parameters to use in locating the peaks corresponding to the labeled polynucleotides of the multiple color calibration standards given the location of a reference peak such as the DR110-labeled peak.

If the mobilities of the labeled polynucleotides of the standard exhibit significant nonlinearities, and the migration of the colored ladder fragments is not easily (and reliably) predictable over a large range of migration times using offsets from one reference peak, the prediction range may be reduced by relying on offsets from neighboring peaks. For example, a polynucleotide labeled with DR110 may be used as a reference peak to locate the polynucleotide (in the same multiple color calibration standard mixture) labeled with DR6G. Subsequently, the polynucleotide labeled with DR6G (in the same standard) may serve as a reference peak to locate the polynucleotide labeled with DTAM. The polynucleotide labeled with DTAM (in the same standard) may then used to locate the polynucleotide labeled with DROX. Finally, the polynucleotide labeled with DROX (in the same standard) may serve as a reference peak to locate the polynucleotide labeled with JAZ.

Peak Detection Parameters

The input parameters of labeled polynucleotides of the multiple color calibration standards for peak detectors may include, but are not limited to:

(a) The starting point and the sample size to be used in estimating the analytical background and the analytical noise in the total emission temporal profile ($\sigma(I)$ in Equation 2.) The analytical background and noise are used to assess the peak S/N ratio.

(b) The threshold variable corresponding to k in Equation 3. This determines the sensitivity of the peak detector to baseline variations.

(c) The threshold variable to be used in detecting baseline segments to the left of peak starting points and to the right of peak ending points, where available. Typically, this is a value less than that used for detecting peak starting points (d) Minimum peak width and peak S/N ratio requirements. These two parameters are selected such that spikes and non-target peaks are ignored. Ideally, only the peaks corresponding to the fragments of the colored ladder are retained by the peak detector.

(e) Reference peak migration time and its tolerance. If this parameter is zero, the last peak found is by default the reference peak.

(f) Migration time offsets of the colored ladder fragment peaks and their tolerances.

(g) The appropriate search windows for maxima and baseline values for the emission temporal profiles.

(h) Number of the colored ladder fragment peaks and the maximum number of peaks expected to be found in the total emission temporal profile. These parameters are used for memory management.

Estimation of Dyes' Reference Spectra

The process of spectral calibration of fluorescent polynucleotide separation apparatus using multiple color calibration standard may include the step of the estimating (extracting) of the dyes' reference spectra from the acquired data matrix, D, using information from the peak detection process. As stated earlier, the rows of the data matrix, D, contain the spectral information. Any spectrum acquired during any data collection/acquisition period can be estimated from the net analytical signals obtained in the spectral channels/bins. A spectrum is, thus, a background/baseline corrected row of D.

The dyes' reference spectra are, therefore, estimated from the corrected rows of D that correspond to data points along the peak segments of the total emission temporal profile. The peak maximum is the data point (row of D) recommended for estimating the dyes' reference spectra. Since the emission temporal profiles of the individual spectral channels/bins are not expected to be perfectly parallel, a row of D is corrected by estimating the net analytical signal in each spectral channel/bin using the peak detection information from the total emission temporal profile and appropriate search windows. Spectral calibration-reference spectra are, also, normalized such that the maximum spectral intensity in each spectrum is set to equal 1. This is accomplished by dividing all corrected spectral intensities in each spectrum by the maximum corrected spectral intensity found in the spectrum.

Uncertainties in Dyes' Reference Spectra

The spectral intensity in a particular channel/bin of a normalized dye's reference spectrum can be expressed as:

$$R_i = I_i/I_m \qquad (4)$$

where $R_i$ is the normalized spectral intensity in the reference spectrum at the ith spectral channel/bin, $I_i$ is the net analytical signal in the ith spectral channel/bin, and $I_m$ is the highest net analytical signal in the spectrum.
The uncertainty in $R_i$ is given according to:

$$\sigma^2(R_1)/R_1^2 = (\rho^2/I_i^2)[1+m^2] \qquad (5)$$

where m is given as $I_i/I_m$, and $\sigma^2$ the variance in the spectral intensities and is assumed to be equivalent in both spectral channels/bins.

The relative error in $R_i$ may be expressed according to:

$$\sigma(R_i)/R_i = [1/SNR_i][1+m^2]^{1/2} \qquad (6)$$

where $SNR_i$ is the signal-to-noise ratio of the net analytical signal in the ith spectral channel/bin.

The term $[1+m^2]$ in Equations 5 and 6 never exceeds the value of 2 according to the normalization defined by Equation 4. The relative error in $R_i$ can, therefore, be expressed as:

$$\sigma(R_i)/R_i \leq [1/SNR_i]\sqrt{2} \qquad (7)$$

where $SNR_i$ is the signal-to-noise ratio of the net analytical signal in the ith spectral channel/bin.

The analytical implication of Equation 6 (and Equation 7) is that the quality of the dyes' reference spectra increases (i.e., the relative errors in the spectral bins decreases) as the signal-to-noise ratio of the net analytical signal increases. The reliability of spectral estimation is determined primarily by the signal-to-noise ratio, not by the number of spectra being used to obtain an average estimate. Since the spectra acquired at peaks' maxima have the highest S/N ratio, these spectra are the preferred spectra to be selected as reference spectra as they are expected to have the lowest relative errors. However, other spectra that substantially correspond to the peak maxima may also be used as reference spectra.

Other embodiments of the invention include systems for separating and detecting fluorescently labeled polynucleotides, wherein the system is designed for spectral calibration in accordance with the subject calibration methods employing multiple color calibration standards. The subject systems comprise a fluorescent polynucleotide separation apparatus and a computer in functional combination with the apparatus. The term "in functional combination" is used to indicate that data from the fluorescent polynucleotide separation apparatus, such data including fluorescence intensity data over a range of detection wavelength and the associated temporal data, is transferred to the computer in such a form that the computer may use the data for calculation purposes. The computer in the system of the invention is programmed to perform the spectral calibration method of the invention using the data produced from running a multiple color spectral calibration standard. Thus the computer is programmed to produce a total emission temporal profile from the spectral and temporal data obtained from the calibration run. The computer may also be programmed to detect peaks in the total emission temporal profile, and determine reference spectral profiles of the dyes attached to the labeled polynucleotide represented by the peaks. A wide variety of computers may be used in the subject system. Typically, the computer is a microprocessor and the attendant input, output, memory, and other components required to perform the necessary calculations. The computers may be generally programmable so as to facilitate modifications or the apparatus of the computer program may be in the form of "firmware" that is not readily subjected to modification.

Other embodiments of the invention include systems for calibrating a fluorescent polynucleotide separation apparatus. The calibration systems includes computer code that receives a plurality of spectral and temporal data from a fluorescent polynucleotide separation apparatus. The system also comprises computer code that calculates a total emission temporal profile from the spectral and temporal data. The system may further comprise additional computer code for performing the subject methods of spectral calibration. Such additional code includes code for detecting peaks, and code for preparing a spectral profile for each of the dyes included in a calibration standard. As the computer code of the subject system requires a physical embodiment to function, the system also comprises a processor and computer readable medium (e.g. optical or magnetic storage medium) for storing the computer program code. The computer readable medium is functionally coupled to the processor.

Another aspect of the invention is methods and compositions for detecting the flow of electrical current through a separation channel of a fluorescent polynucleotide separation apparatus. Such methods and compositions are particularly useful with fluorescent polynucleotide separation apparatus that employ multiple separation channels, e.g. a multi capillary or multiple microchannel system, because of interruptions in current flow in individual separation channels may be difficult to detect if a substantial percentage of the channels have proper current flow. The subject electrical flow monitoring methods involve the use of fluorescent dyes that are spectrally distinct from fluorescently labeled polynucleotides of primary interest. These spectrally distinct fluorescent dyes are referred to herein as monitoring dyes. In a preferred embodiment of the invention, the monitoring dye is selected so as to produce significant emission when excited by the same excitation source or sources used to excite the other fluorescent dyes in the composition of interest.

For example, a polynucleotide sequencing reaction product mixture (chain termination sequencing) may contain (1) four spectrally distinct fluorescent dyes, wherein each of the four dyes is correlated with a different polynucleotide base (e.g. fluorescently labeled dideoxy sequencing) and (2) a monitoring dye that is spectrally distinct from the four other dyes. Movement of the monitoring dye in a separation channel can be used to confirm that current flow and therefore proper separation of the sequencing reaction products is occurring. Monitoring dyes may be used in conjunction with sequencing reaction mixtures that employ either more or less than four dyes.

Another aspect of the invention is methods and compositions for detecting the flow of electrical current through a separation channel of a fluorescent polynucleotide separation apparatus. Such methods and compositions are particularly useful with fluorescent polynucleotide separation apparatus that employ multiple separation channels, e.g. a multi capillary or multiple microchannel system, because of the possibility of failure of a subject separation channel. The subject electrical current flow monitoring methods involve the use of fluorescent dyes that are spectrally distinct from fluorescently labeled polynucleotides of primary interest. These spectrally distinct fluorescent dyes are referred to herein as monitoring dyes. In a preferred embodiment of the invention, the monitoring dye is selected so as to produce significant emission when excited by the same excitation source or sources used to excite the other fluorescent dyes in the composition of interest.

For example, a polynucleotide sequencing reaction product mixture (chain termination sequencing) may contain (1) four spectrally distinct fluorescent dyes, wherein each of the four dyes is correlated with a different polynucleotide base (e.g. fluorescently labeled dideoxy sequencing) and (2) a monitoring dye that is spectrally distinct from the four other dyes. Movement of the monitoring dye in a separation channel can be used to confirm that current flow and therefore proper separation of the sequencing reaction products is occurring. Monitoring dyes can be used in conjunction with sequencing reaction mixtures that employ either more or less than four dyes, e.g., one color or two color based sequencing.

Monitoring dyes may also be used in conjunction with other forms of fluorescent polynucleotide fragment analysis in addition to polynucleotide sequencing. Such other forms of analysis include nucleic acid amplification products, ligation products, and the like.

The monitoring dyes may be used by themselves or may be conjugated to other molecules that can modify the migration rate of the monitoring dyes during electrophoresis, i.e., a mobility modifier. Examples of such migration modifying molecules include polynucleotides, polynucleotide analogs, peptides, polypeptides, the mobility modifying molecules described in U.S. Pat. No. 5,514,543, and the like. Preferably, these mobility modifying molecules are selected so as to not have spectral properties that interfere with fluorescent detection of the dyes of interest. Detailed descriptions of how to conjugate fluorescent dyes to various compounds can be found in, among other places, Hermanson, *Bioconjugate Techniques*, Academic Press, San Diego, Calif. (1996). Unless indicated otherwise by context of usage, the term "monitoring dye" includes monitoring dye conjugates.

Embodiments of the invention include compositions comprising fluorescently labeled polynucleotides and one or more monitoring dyes, wherein the monitoring dyes are spectrally distinct from the other fluorescent dyes in the mixture. The monitoring dyes may be added to the composition either before, after, or during the formation of the fluorescently labeled polynucleotides for analysis. For example, a monitoring dye may be added to a polynucleotide sequencing reaction either before or after the reaction is terminated. In some embodiments of the invention, the subject compositions comprise multiple different monitoring dyes. In such embodiments, the monitoring dyes are preferably conjugates having different electrophoretic mobilities. In other embodiments of the subject compositions, a single signal fluorescent dye is present, but the dye molecules are conjugated to two or more different mobility modifier species so as to produce multiple opportunities to detect the monitoring dye during electrophoretic separation.

The invention also includes methods of detecting the flow of electrical current through a separation channel of a fluorescent polynucleotide separation apparatus by introducing a fluorescently labeled polynucleotide composition into a channel of a fluorescent polynucleotide separation apparatus. The fluorescently labeled polynucleotide composition comprises a polynucleotide labeled with a first fluorescent dye and a monitoring dye that is spectrally distinct from the first fluorescent dye. In most embodiments of the invention, the fluorescently labeled polynucleotide is a complex mixture of different length polynucleotides. Exemplary of such fluorescently labeled polynucleotide mixtures are the products of DNA sequencing reactions employing either fluorescently labeled primers or fluorescently labeled terminators, PCR amplification products formed by using fluorescently labeled primers, fluorescently labeled mini-sequencing reactions, products, fluorescently labeled oligonucleotide ligation reaction products, and the like. Such reactions produce genetic information that may be analyzed in the fluorescent polynucleotide separation apparatus. The monitoring dye is spectrally distinct from the fluorescent dyes used to label the polynucleotides that convey genetic information. For example, the invention includes a composition comprising a complex mixture of different fluorecently labled polynucleotides produced from four color chain termination sequencing and signal dye that is spectrally distinct from the four fluorescent dyes on the different sequencing reaction products.

After the fluorescently labeled polynucleotide composition is introduced in the separation channel of a fluorescent polynucleotide separation apparatus, the apparatus is activated and the polynucleotide (and signal dyes, if not joined to a polynucleotide) permitted to separate along the separation channel. The movement of the monitoring dye through the separation channel may then be detected by the apparatus. Lack of movement of the monitoring dye (or dyes) or permutations of the movement of the monitoring dyes through the separation channels may be used to detect problems with the flow of electrical current through the separation channel. The movement of monitoring dyes in different channels of a multiple channel fluorescent polynucleotide separation apparatus may be compared with one another so as to facilitate the detection of problems with current flow.

Embodiments of the invention also include computer code for using monitoring dyes to monitor current flow in the subject methods, computer storage media embodying such code, and programmable electronic computer programmed with such code.

INCORPORATION BY REFERENCE

All publications, patent applications, and patents referenced in the specification are herein incorporated by reference to the same extent as if each individual publication or patent application was specifically and individually indicated to be incorporated by reference.

EQUIVALENTS

All publications, patent applications, and patents mentioned in this specification are indicative of the level of skill of those skilled in the art to which this invention pertains.

Although only a few embodiments have been described in detail above, those having ordinary skill in the molecular biology art will clearly understand that many modifications are possible in the preferred embodiment without departing from the teachings thereof. All such modifications are intended to be encompassed within the following claims. The foregoing written specification is considered to be sufficient to enable skilled in the art to which this invention pertains to practice the invention. Indeed, various modifications of the above-described modes for carrying out the invention which are apparent to those skilled in the field of molecular biology or related fields are intended to be within the scope of the following claims.

What is claimed is:

1. A method comprising:

introducing a fluorescent polynucleotide separation standard into a fluorescent polynucleotide separation apparatus, wherein the standard comprises at least two polynucleotides of different length, each of the polynucleotides being labeled with a spectrally distinct fluorescent dye, separating the polynucleotides from each other, detecting the separated polynucleotides with a detector, wherein the detector collects spectral data from the separated polynucleotides over a plurality of spectral channels, collects temporal data from the separated polynucleotides over a plurality of temporal points, and generating a total emission temporal profile from the spectral and temporal data.

2. The method according to claim 1, wherein the separation standard comprises four polynucleotide each of different length and labeled with a spectrally distinct dye.

3. The method of claim 2, wherein the polynucleotides are of a lengths that minimize the spectral overlap of the fluorescent dye at each point of detection for the polynucleotides.

4. The method according to claim 1, wherein the separation standard comprises five polynucleotide each of different length and labeled with a spectrally distinct dye.

5. The method of claim 1, further comprising:

using the total emission temporal profile, calibrating the apparatus.

6. A system for separating and detecting fluorescently labeled polynucleotides comprising, fluorescent polynucleotide separation apparatus, a computer in functional combination with the fluorescent polynucleotide separation apparatus, wherein the computer is programmed to produce a total emission temporal profile from a calibration standard comprising at least two polynucleotides of different length, each of the polynucleotides being labeled with a spectrally distinct fluorescent dye.

7. The system according to claim 6, wherein the computer is programmed to detect the peaks in the total emission temporal profile.

8. The system according to claim 7, wherein a reference spectrum for each of the fluorescent dyes is produced by selecting a reference spectrum that substantially corresponds to a peak of the emission temporal profile.

9. The system according to claim 8 wherein the computer corrects each reference spectrum is by estimating the net analytical signal for each spectral channel.

10. A method comprising:

introducing a fluorescent polynucleotide separation standard into a fluorescent polynucleotide separation apparatus, wherein the standard comprises at least two polynucleotides of different length, each of the polynucleotides being labeled with a spectrally distinct fluorescent dye, separating the polynucleotides from each other, detecting the separated polynucleotides with a detector, wherein the detector collects spectral data from the separated polynucleotides over a plurality of spectral channels, and collects temporal data from the separated polynucleotides over a plurality of temporal points, generating a data matrix comprising said spectral and temporal data, generating a total emission temporal profile from the spectral and temporal data of said matrix, detecting peaks in the total emission temporal profile, and using the detected peaks, estimating reference spectral profiles of the dyes, whereby the apparatus is calibrated.

* * * * *